United States Patent [19]

Baggiolini et al.

[11] Patent Number: 4,898,855

[45] Date of Patent: Feb. 6, 1990

[54] DEUTERATED ANALOGS OF 1,25-DIHYDROXYCHOLECALCIFEROL

[75] Inventors: Enrico G. Baggiolini, North Caldwell; Bernard M. Hennessy, Nutley; Milan R. Uskokovic, Upper Montclair, all of N.J.

[73] Assignee: Hoffman-La Roche Inc., Nutley, N.J.

[21] Appl. No.: 96,981

[22] Filed: Sep. 14, 1987

[51] Int. Cl.$^4$ ............................ A61K 31/59; C07J 9/00
[52] U.S. Cl. .................................... 514/167; 260/397.2; 556/436; 560/119; 568/374; 568/819
[58] Field of Search ....................... 514/167; 260/397.2

[56] References Cited

U.S. PATENT DOCUMENTS

| | | | |
|---|---|---|---|
| 4,225,596 | 9/1980 | DeLuca ............................... | 514/167 |
| 4,269,777 | 5/1981 | DeLuca et al. .................. | 260/397.1 |
| 4,297,289 | 10/1981 | DeLuca et al. .................. | 260/397.2 |
| 4,424,161 | 1/1984 | Holick .............................. | 260/397.2 |
| 4,508,651 | 4/1985 | Baggiolini et al. ............... | 260/397.2 |
| 4,804,502 | 2/1989 | Baggiolini et al. ............... | 260/397.2 |

OTHER PUBLICATIONS

Chemical Abstracts, vol. 90, no. 3, Jan. 15, 1979, 17948 W.

American Chemical Society, vol. 18, No. 18, 1979, pp. 3977-3983, Esvelt et al.

FEBS Letters, vol. 94, No. 2, Oct. 1978, pp. 228-230, Redel et al.

American Chemical Society, vol. 18, No. 22, 1979, pp. 4775-4780, Wichmann et al.

*Primary Examiner*—Paul E. Konopka
*Attorney, Agent, or Firm*—George M. Gould; Bernard S. Leon; Matthew Boxer

[57] ABSTRACT

The invention is directed to deuterated vitamin D analogs, and processes and intermediates for their preparation. The end products, that is the deuterated vitamin D analogs, are useful for the treatment osteoporosis and cutaneous inflammations such as psoriasis, and contact dermatitis.

16 Claims, No Drawings

DEUTERATED ANALOGS OF 1,25-DIHYDROXYCHOLECALCIFEROL

BRIEF SUMMARY OF THE INVENTION

The invention is directed to a deuterated analog of 1,25-dihydroxycholecalciferol of the formula

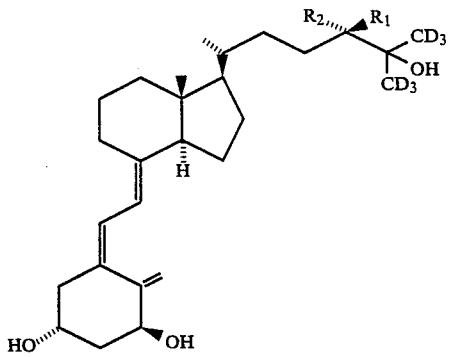

wherein $R_1$ and $R_2$ are both deuterium.

The invention relates to pharmaceutical compositions comprising a compound of formula I wherein $R_1$ and $R_2$ are either both hydrogen or both deuterium.

The compounds of formula I are useful as agents for the treatment of osteoporosis, psoriasis, and contact dermatitis.

The invention also relates to processes for preparing deuterated analogs of 1,25-dihydroxycholecalciferol.

DETAILED DESCRIPTION OF THE INVENTION

As used throughout the specification and the appended claims, the term "lower alkyl" denotes a monovalent substituent consisting solely of carbon and hydrogen of from 1 to 8 carbon atoms which may be straight- or branched-chain. Examples of lower alkyl groups are methyl, ethyl, n-propyl, 1-propyl, tert-butyl, hexyl, heptyl, octyl and the like. The term "aryl" denotes an organic radical derived from an aromatic hydrocarbon by the removal of a hydrogen atom. Exemplary of aryl are phenyl and substituted phenyl. The term "substituted" as applied to "phenyl" refers to phenyl which is substituted with one or more of the following groups: lower alkyl, fluorine, chlorine, bromine, iodine, nitro, cyano, trifluoromethyl and the like. The term "aryl-lower alkyl" denotes a lower alkyl as defined above which is substituted by aryl as defined above. The term "protecting or derivatizing group" denotes a chemical moiety conventionally employed to protect hydroxy groups. Exemplary of such protecting groups are —(CO)-lower alkyl and tri-lower alkylsilyl.

In the formulas herein, the various substituents are illustrated as joined to the nucleus by one of the following notations. A dark line (———) indicates that a substituent is in the β-orientation, (that is, above the plane of the molecule), a broken line (----) indicates that a substituent is in the α-orientation (that is, below the plane of the molecule), and a wavy line (∼∼∼) indicates that a substituent may be in either the α or β orientation or a mixture of compounds containing substituents in the α and/or β orientation.

The invention is directed to a deuterated analog of 1,25-dihydroxycholecalciferol of the formula wherein $R_1$ and $R_2$ are both deuterium.

The invention relates to pharmaceutical compositions comprising a compound of formula I wherein $R_1$ and $R_2$ are either both hydrogen or both deuterium.

The compounds of formula I are useful as agents for the treatment of osteoporosis, psoriasis, and contact dermatitis.

The compound of formula I wherein $R_1$ and $R_2$ are both hydrogen is 26,26,26,27,27,27-hexadeutero-1α,25-dihydroxycholecalciferol, which is referred to as the "hexadeutero" compound.

The compound of formula I wherein $R_1$ and $R_2$ are both deuterium is 24,24,26,26,26,27,27,27-octadeutero-1α,25-dihydroxycholecalciferol, which is referred to as the "octadeutero" compound. The invention also relates to pharmaceutical compositions comprising a mixture of the hexadeutero compound and the octadeutero compound.

The invention also relates to processes for preparing deuterated analogs of 1,25-dihydroxycholecalciferol.

The invention also relates to intermediates of the formula

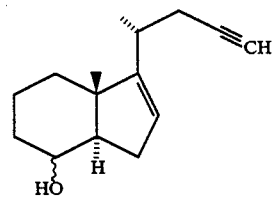

In particular, the invention relates to the intermediate of formula V, [3aS-[3(R*),3aα,7β,7aβ]]-3a,4,5,6,7,7a-hexahydro-3a-methyl-3-(1-methyl-3-butynyl)-1H-indene-7-ol.

The invention also relates to intermediates of the formula

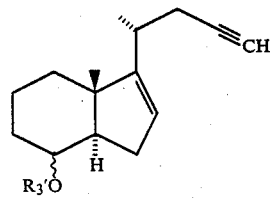

wherein $R_3'$ is Si(Alk)$_3$ wherein Alk is lower alkyl.

In particular, the invention relates to the intermediate of formula VI, [3aS-[3(R*),3aα,7β,7aβ]]-3a,4,5,6,7,7a- hexahydro-3a-methyl-3-(1-methyl-3-butynyl)-7-[(trimethylsilyl)oxy]-1H-indene.

The invention also relates to intermediates of the formula

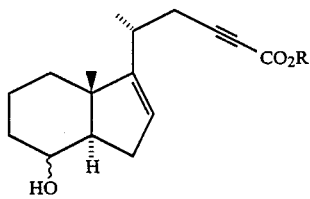

VII wherein R is lower alkyl, aryl or aryl-lower alkyl.

Preferred among intermediates of formula VII are those wherein R is lower alkyl.

Exemplary of compounds of formula VII is, [3aS-[3(R*),3aα,7β,7aβ]]-5-(3a,4,5,6,7,7a-hexahydro-7-hydroxy-3a-methyl-1H-inden-3-yl)-5-methyl-2-pentynoic acid methyl ester.

The invention also relates to intermediates of the formula

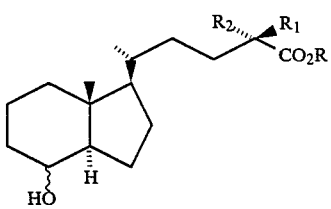

VIII wherein $R_1$ and $R_2$ are either both hydrogen or deuterium, and R is lower alkyl, aryl or aryl-lower alkyl.

In particular, the invention relates to the intermediate of formula VIII, [1R-[1α(R*),3aβ,4β,7aα]]octahydro-δ,7a-dimethyl-4-hydroxy-1H-indene-1-pentanoic acid methyl ester.

The invention also relates to intermediates of the formula

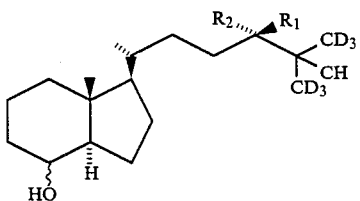

IX wherein $R_1$ and $R_2$ are either both hydrogen or deuterium.

In particular, the invention relates to an intermediate of formula IX, [1R-[1α(R*),3aβ,4β,7aα]]-octahydro-ε,7a-dimethyl-β,β-d$_2$-α,α-(dimethyl-d$_3$)-4-hydroxy-1H-indene-1-pentanol.

The invention also relates to intermediates of the formula

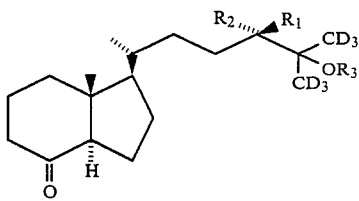

X wherein $R_3$ is hydrogen or Si(Alk)$_3$, Alk is lower alkyl, and $R_1$ and $R_2$ are either both hydrogen or deuterium.

In particular, the invention relates to the intermediate of formula X, [1R-[1α(R*),3aβ,7aα]]octahydro-1-[5-[(trimethylsilyl)oxy]-1-methyl-5-(methyl-d$_3$)-4,4,6,6,6-d$_5$-hexyl]-7a-methyl-4H-inden-4-one.

The invention also relates to an intermediate of the formula X, [1R-[1α(1R*),3aβ,7aα]]-octahydro-1-[5-[(trimethylsilyl)oxy]-1-methyl-5-(methyl-d$_3$)-6,6,6-d$_3$-2-hexyl]-7a-methyl-4H-inden-4-one;

The invention also comprises a process for the preparation of a compound of the formula

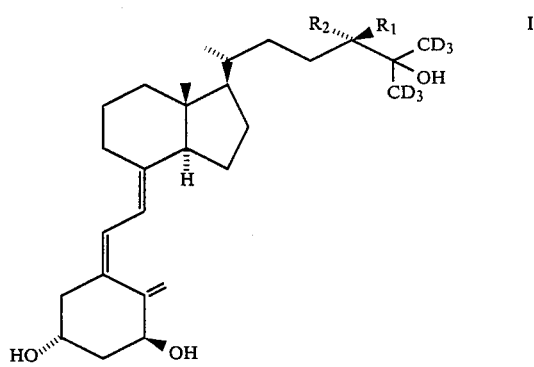

I wherein $R_1$ and $R_2$ are either both hydrogen or both deuterium.

A compound of formula I can be prepared by reacting a compound of formula

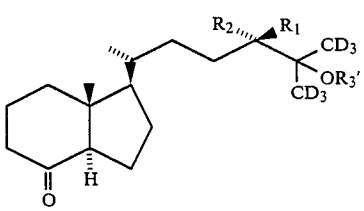

Xa wherein $R_1$ and $R_2$ are both hydrogen or deuterium and $R_3'$ is as described above with a compound of the formula

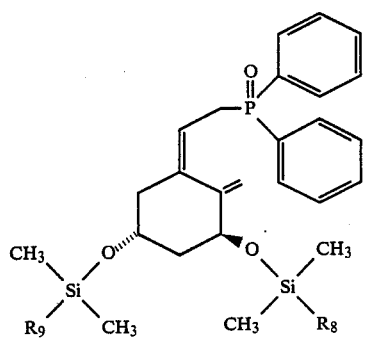

wherein $R_8$ and $R_9$ are lower alkyl or aryl to obtain a compound of formula

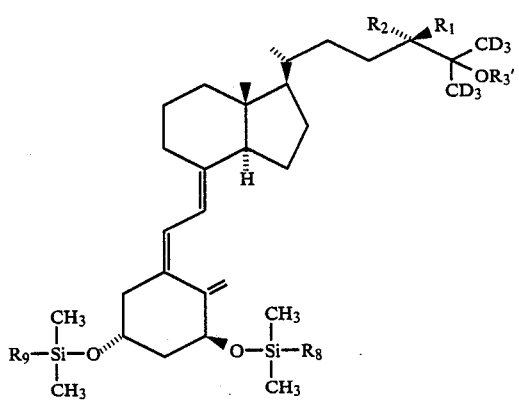

wherein $R_1$, $R_2$, $R_3'$, $R_8$, and $R_9$ are as described above.

The compounds of formulas XI are known or can be prepared in accordance with known procedures. (See e.g. E. G. Baggiolini, J. A. Iacobelli, B. M. Hennessy, A. D. Batcho, J. F. Sereno, M. R. Uskokovic, J. Org. Chem. 1986, (51), 3098.

The reaction is carried out in the presence of a base in a conventional ether solvent under an inert atmosphere and a temperature in the range of from about −80° C. to about −50° C. Exemplary of suitable bases are alkyl lithium compounds and dialkyl or alkyl substituted disilyl amides. The compound of formula XII can be purified by elution chromatography on silica gel.

A compound of formula XII is then converted to the corresponding cholecalciferol derivative of formula I by removal of the hydroxyl derivatizing groups. This can be achieved, for example, by treatment with a lower alkanol or with mixtures of water and a miscible organic solvent in the presence of an acid. While any mineral acid or lower alkanoic or sulfonic acid may be used it is preferred to use the hydrogen form of a cationic exchange resin (for example, AG 50W-X4 Bio-Rad Laboratories, Amberlite CG120, Rohm and Haas Co. Amerlyst 15 Rohm and Haas Company, Dowex 50X4 Dow Chemical Company) as a suspension in a lower alkyl alcohol. The compound of formula I is isolated by filtering off the solid cationic exchange resin and evaporation of the volatiles under reduced pressure. Alternatively, the deprotection can be carried out by treatment of a compound of formula XII with tetrabutylammonium fluoride at room temperature and in an ether solvent, preferably tetrahydrofuran.

A compound of formula X, which is the starting material in the process of the invention can be prepared by the process hereinafter described.

A compound of formula

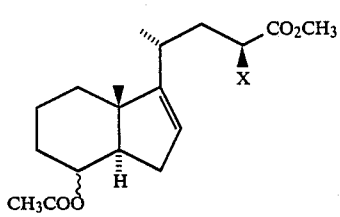

wherein X is chloro or bromo, which is known, or can be prepared according to known procedures, (P. M. Wovkulich, E. G. Baggiolini, B. M. Hennessy, M. R. Uskokovic, E. Mayer, A. W. Norman, J. Org. Chem., 1983, (48), 4433) is reduced by reaction with a hydride reducing agent in an inert organic solvent so as to yield the corresponding alcohol of the formula

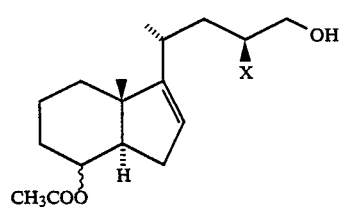

wherein X is as described above.

Exemplary of suitable reducing agents are diisobutyl aluminum hydride, and lithium aluminum hydride with lithium aluminum hydride being especially preferred.

Exemplary of suitable inert organic solvents are depending upon the reducing agent, lower aliphatic hydrocarbon solvents such as hexane, heptane, octane and the like, aromatic hydrocarbons such as benzene and toluene, chloroform, carbon tetrachloride and the like, and conventional ether solvents such diethylether and tetrahydrofuran with tetrahydrofuran being especially preferred for the reduction with lithium aluminum hydride. The foregoing reaction is carried out at a temperature in the range of about −70° C. to about 80° C. with about 0° C. to about room temperature being preferred.

In the next step, an alcohol of formula III is converted to the corresponding halide

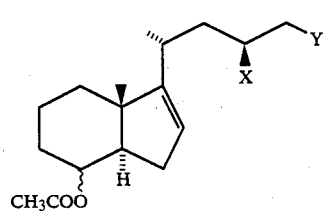

wherein Y is chloro, bromo, or iodo and X is as described above.

This is best carried out in two steps, by first converting an alcohol or formula III to a corresponding compound of formula

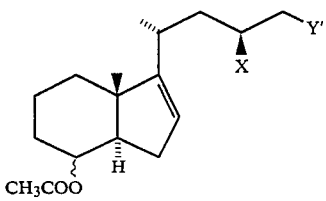

IVa wherein Y' is OSO₂R, R is lower alkyl, aryl or aryl-lower alkyl and X is as described above, and then reacting the compound of formula IVa with a halogenating agent to obtain a compound of formula

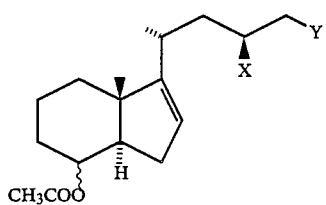

IV wherein X and Y are described above.

Exemplary of halogenating agents are lithium chloride or more preferably lithium bromide in a polar organic solvent such as acetone, acetonitrile or N,N-dimethylformamide, at a temperature in the range of about 25° C. to about 100° C.

In the next step a compound of formula IV is reacted in a polar organic solvent under an inert atmosphere and in the presence of a strong base to yield a compound of formula.

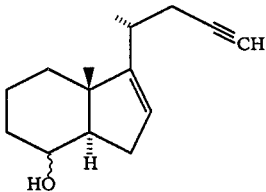

V

Exemplary of the strong base are lithium hydride, sodium hydride, potassium amide, or more preferably sodium amide in the presence of tert.-butyl alcohol. Exemplary of the polar organic solvent is dimethylformamide or more preferably hexamethylphosphoramide. The reaction is conducted at −20° C. to about 30° C. with room temperature being preferred.

In the next step, an alcohol of formula V is reacted with a silylating agent such as a 1-(trialkylsilyl)imidazole, preferably 1-(trimethylsilyl)imidazole, in a conventional ether solvent such as diethylether or more preferably tetrahydrofuran at −20° C. to about 30° C., more preferably at about room temperature so as to yield a compound of formula

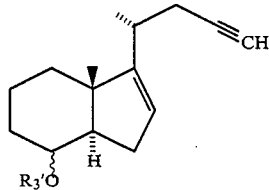

VI wherein R₃' is Si(Alk)₃ wherein Alk is lower alkyl.

A compound of formula VI is then reacted with a strong base such as sodium hydride, potassium amide, n-butyllithium, or lithium dialkylamine in an aprotic solvent such as hexane, diethylether or tetrahydrofuran at a temperature in the range of about −100° C. to about room temperature, preferably about −78° C., followed by treatment with an alkyl-, aryl-, or aryl-lower alkyl chloroformate, preferably methyl chloroformate to yield after work up a compound of formula

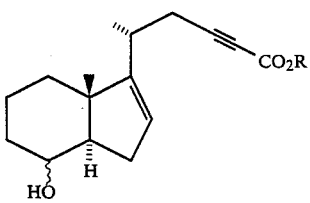

VII wherein R is as described above.

In the next step, a compound of formula VII is catalytically hydrogenated by reaction with hydrogen in the presence of a hydrogenation catalyst in a suitable organic solvent at a temperature in the range of about 0° C. to about 80° C. with room temperature and atmospheric pressure preferred so as to yield a compound of formula

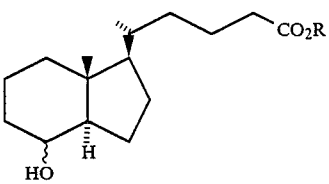

VIIIa wherein R is as described above.

Exemplary of suitable hydrogenation catalysts are 5 to 10 percent rhodium on carbon, platinum oxide, and 5 to 10 percent palladium on carbon, with 5 percent palladium on carbon being especially preferred. Exemplary of suitable solvents are conventional ether solvents such as diethylether and tetrahydrofuran, aromatic hydrocarbon solvents such as benzene and toluene, alkanoic acid alkyl esters such as ethylformate or ethylacetate, and lower alkyl alcohols such as methanol, ethanol, propanol and the like, with ethanol being especially preferred.

Compounds of formula VIIIa which are intermediates in the claimed processes, are also an aspect of the invention.

In the next step, a compound of formula VIIIa may be reacted with methyl lithium-d₃ in a conventional ether solvent such as anhydrous tetrahydrofuran, or more preferably anhydrous diethylether, at a temperature in a range of about −30° C. to about 30° C. with 0°

C. being especially preferred, under an inert atmosphere to form a compound of formula

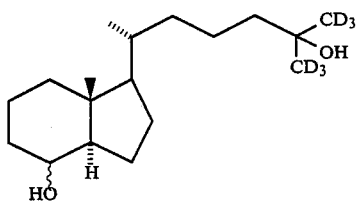

IXa

In the next step, a compound of formula IXa is reacted with an oxidative agent such as pyridinium chlorochromate in a lower alkyl halide solvent such as chloroform, carbon tetrachloride, or more preferably dichloromethane, at a temperature in a range −10° C. to 30° C. with room temperature being especially preferred. The compound which results from this oxidation step is the ketone

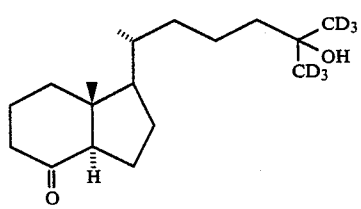

IXa'

After the reaction mixture is worked up by conventional means it is treated with a silylating agent such as a 1-(trialkylsilyl)imidazole like 1-(trimethylsilyl)imidazole in an inert organic solvent such as an ether or a halogenated hydrocarbon like dichloromethane, under an inert atmosphere, to yield a compound of the formula

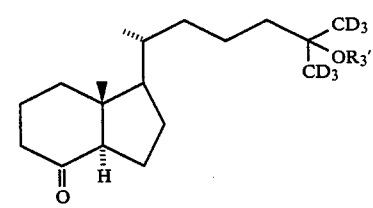

Xa wherein $R_3'$ is as described above.

As can be seen, a compound of formula Xa is encompassed by formula X. The conversion of a compound of formula X to a compound of formula I has been described above.

Alternatively, a compound of formula VIIIa can be deuterated so as to yield a compound of formula

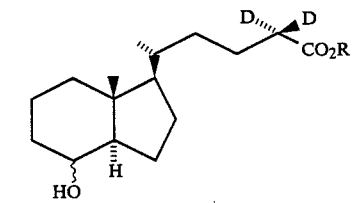

VIIIb wherein R is as described above by reaction with methyl-$d_3$-alcohol-d in the presence of sodium methoxide-$d_3$ under an inert atmosphere at a temperature in the range of about 0° to 80° C. with about 50° C. being preferred.

The subsequent conversion of a compound of formula VIIIb to a compound of formula Xb is analogous to the conversion of compound of formula VIIIa to a compound of formula Xa.

The following intermediate compounds, in the order in which they appear, are synthesized in the conversion of a compound of formula VIIIb to a compound of formula Xb.

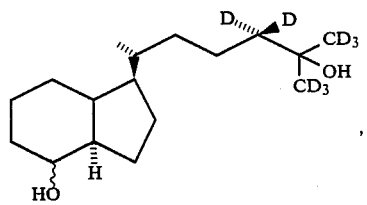

IXb and then

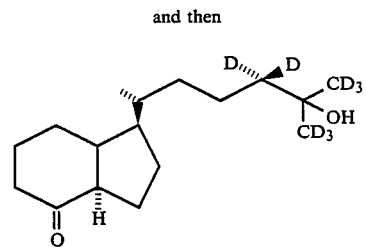

IXb'

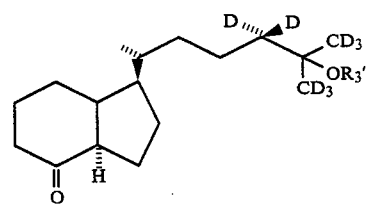

Xb wherein $R_3'$ is as described above.

As can be seen, a compound of formula Xb is encompassed by formula X. The conversion of a compound of formula X to a compound of formula I has been described above.

It can also be seen from the above that compounds of formulas VIIIa and VIIIb are encompassed by formula VIII; and compounds of formula IXa and IXb are encompassed by formula IX.

The compounds of formula I can be administered in dosages that are in the range of about 0.25 μg to 2 μg per day, to warm-blooded animals in need thereof, for the treatment of disease states such as osteoporosis, and cutaneous inflammations such as psoriasis, and contact dermatitis. The compounds of formula I can be administered in a range of about 0.25 to 2 μg per day for the treatment osteoporosis. The compounds of formula I can be administered orally, subcutaneously, intramuscularly, intravenously or intraperitoneally in the treatment of osteoporosis. In the treatment of psoriasis, or contact dermatitis compounds of formula I can also be administered topically.

The useful activity of compounds of formula I can be demonstrated utilizing, for instance, the test procedures which follow:

STIMULATION OF THE AVIAN AND PORCINE CARTILAGE GROWTH IN VITRO

METHODS

Experimental Procedures

Organ culture of embryonic pelvic cartilage was performed using previously described methods Burch WM, Lebovitz HE (1982) "Triiodothyronine stimulation of in vitro growth and maturation of embryonic chick cartilage." *Endocrinology* 111: 462 and Burch WM, Lebovitz HE (1981) "Adenosine 3',5'-monophosphate: A modulator of embryonic chick cartilage growth" *J. Clin. Investig.* 68: 1496. Briefly, pelvic cartilages from 9 to 10-day chick embryos were removed, cleaned aseptically, individually placed in 30 mm plastic wells which had 2 ml of $BGJ_b$. (Fitton-Jackson modification) medium containing 0.5% recrystallized bovine serum albumin, and incubated in an atmosphere of 10% $CO_2$—90% room air at 37° C. No antibiotics or serum were added to the medium. Albumin was included to prevent non-specific adsorption of the steroids to the plastic wells. At the end of three days incubation, cartilage wet and dry weight were determined. In each experiment, 12 rudiments (n=12) were used for control and for each vitamin D analog. The vitamin D analogs were weighed, diluted in propanol, and added at the initiation of the three-day incubation.

Estimates of collagen and proteoglycan synthetic rates were obtained by assessing radiolabeled precursor incorporation. A large percentage increase in a particular radiolabeled precursor shows a large synthetic rate of cartilage formation. The cartilages were pulsed with 2 $\mu$Ci [$^3$H]-proline or 2 $\mu$Ci [$^3$H]-thymidine and 0.2 $\mu$Ci of $H_2$ $^{35}SO_4$ during the final 12 hours of the 3-day incubation, removed, and wet weight recorded. Then the cartilages were rinsed in 5% trichloroacetic acid (TCA), equilibrated in 4 ml TCA overnight, air dried to constant weight, and dry weight determined. The cartilages were solubilized in Protosol and acid-insoluble counts representing [$^3$H]-proline into collagen and $^{35}SO_4$ into proteoglycan (Eisenbarth GS, Beuttel Sc, Lebovitz HE (1973) Fatty acid inhibition of somatomedin (serum sulfutin factor) stimulated protein and RNA synthesis in embryonic chicken cartilage" *Biochim Biophys Acta* 331: 397) assessed by liquid scintillation spectrophotometry and expressed as CPM/cartilage.

Organ cultures of growth-plates from the scapula cartilages of fetal pigs were performed using methods previously described. (Burch WM, Lebovitz HE (1982) "Triiodothyronine stimulates maturation of porcine growth-plate cartilage in vitro." *J. Clin. Investig.* (70: 496.) Growth-plates (n=12/treatment group) were isolated aseptically, wet weight obtained, and then placed into individuals wells of 24 well-plastic culture plates. Growth-plates were incubated in 1.5 ml of MEM (Joklik-Modified) containing 0.5% BSA for 14–17 days. The medium was changed and fresh additives introduced every 4–5 days. This medium (MEM) was chosen because it contained antibiotics which allowed relatively long-term culture without contamination. $BGJ_b$. (Fitton-Jackson modification) medium with addition of antibiotics has also been used with similar results. At the end of the incubation, growth-plates were weighed for wet weight, then air dried for dry weight. The change in growth-plate wet weights were determined and the cartilages were photographed.

Materials: $BGJ_b$. (Fitton-Jackson modification) (Cat #320-1591) medium and Minimal Essential Medium (Joklik-Modified) (Cat #410-1300) were obtained from Grand Island Biological Co. (Grand Island, NY) and tissue culture plates (Linbro 76-058-05 & 76-033-05) from Flow Laboratories (McLean, VA). [$^3$H]-Proline (38.5 Ci/mmol), [$^3$H]-methylthymidine (40 Ci/mmol), $H_2$[$^{35}SO_4$] (35 Ci/mmol), and Protosol were obtained from New England Nuclear (Boston, MA). Bovine serum albumin was purchased from Reheis, Armour Pharmaceutical Co. (Kankakee, Ill.).

The results of these tests are set forth in Table I just below.

TABLE I

| Compound | CONCEN- TRATION M | AVIAN CARTILAGE IN VITRO % INCREASE | | | | PORCINE CARTILAGE IN VITRO % INCREASE | | |
|---|---|---|---|---|---|---|---|---|
| | | DRY WEIGHT | $^3$H THYMIDINE | $^3$H PROLINE | $^{35}$S | DRY WEIGHT | $^3$H PROLINE | $^{35}$S |
| 1,25-(OH)$_2$D$_3$ | $10^{-9}$ | 31.8 | | | | 49 | 300 | 280 |
| | $10^{-10}$ | 27.2 | | 122 | 21.8 | 0 | 0 | 0 |
| | $10^{-11}$ | 24.1 | | 68.3 | 13.8 | 0 | 0 | 0 |
| | $10^{-12}$ | 22.6 | | 46.3 | 8.6 | | | |
| 1,25-(OH)$_2$D$_3$-Hexa$^2$H | $10^{-9}$ | 35.3 | | 148.3 | 41.0 | | | |
| | $10^{-10}$ | 29.1 | 44.3 | 145.4 | 30.1 | 57.6 | 215.7 | 466.0 |
| | $10^{-11}$ | 29.8 | | 131.4 | 26.3 | 40.9 | 123.6 | 203.2 |
| | $10^{-12}$ | 31.2 | 62.5 | 65.0 | | 31.5 | | |
| | $10^{-13}$ | 20.5 | 57.9 | 36.0 | 21.5 | 29.5 | | |
| 1,25-(OH)$_2$D$_3$-Octa$^2$H | $10^{-9}$ | 28.0 | | | 10.8 | 60 | 150 | 490 |
| | $10^{-10}$ | 21.6 | 25.0 | | | 50 | 75 | 410 |
| | $10^{-11}$ | 17.0 | 20.7 | | | 42 | 20 | 95 |
| | $10^{-12}$ | 10.3 | 15.3 | | | | | |

STIMULATION OF INTESTINAL CALCIUM ABSORPTION AND BONE CALCIUM MOBILIZATION IN RAT

Experimental Procedures

Male weanling rats (Holtzman, Madison WI.) were housed individually in overhanging wire cages and were fed a vitamin D-deficient diet containing low calcium (0.005%) and normal phosphorus (0.3%). Test compounds were dissolved in 10–20 $\mu$l of ethanol. Plasma (1.8 ml), collected from vitamin D, deficient rats was added to the ethanol solution. The test compounds were given intrajugularly in 0.3 ml of the ethanol-plasma carrier solution. Controls received carrier alone.

Eighteen hours after injection, the rats were decapitated and their duodena were used to measure intestinal $^{45}$Ca transport (ICA) by the everted gut sac technique. The duodena were prepared by dissecting free the first 10 cm of the intestine distal to the pyloric valve. The tissue was immediately rinsed with cold 0.9% saline. After rinsing, as much mesentery that could be removed was trimmed free and the intestine everted in a manner such that the distal end remained tied to the everting rod. The intestine was ligated just distal to the pyloric valve. It was then cut to a length of 5.5 cm, and filled with 0.6 ml of incubation buffer. The sac was tied off and placed in a 25 ml flask containing 10 ml of incubation buffer and incubated at 37° C. for 90 minutes. The flask was continuously gassed with 95/5 $O_2/CO_2$. At termination of the experiment the contents of the sac were drained into a test tube and a portion was counted for $^{45}Ca$ presence. An aliquot of the buffer from the incubation flask was also counted for radioactive $^{45}Ca$. Data were expressed as the ratio (S/M) of the tracer concentration in the serosal (S) media (inside the sac) to the concentration of the tracer in the mucosal (M) media (outside the sac).

Bone Ca resorption (BCR) was estimated by mesuring the blood Ca increase in the treated rats. Blood was collected in heparinized tubes and centrifuged. The treated cytosol was centrifuged at 20,000 × g for 10 minutes. The supernatant was discarded and the pellet lyophilized and stored at −70° C. Prior to binding assay the pellet was resuspended in cold binding assay buffer containing 150 mM KCl, 50 mM $NaPO_4$, 1.5 mM EDTA and 5 mM dithiothreitol. The receptor was prepared in such a manner that 50% of the 1,25-$(OH)_2[^3H]D_3$ was specifically bound in the presence of 200 pM (40 pg/tube) non-radioactive 1,25-$(OH)_2D_3$. Results of test compounds were related to 1,25-$(OH)_2D_3$ using the following formula:

$$\frac{a}{b} \times 100$$

where a is the quantity of 1,25-$(OH)_2D_3$ that will displace 50% of the 1,25-$(OH)_2[^3H]D_3$ and b is the amount of test compound that will displace 50% of the 1,25-$(OH)_2[^3H]D_3$.

Results of the above tests are contained in Table II below.

TABLE II

| | | % of 1,25-$(OH)_2D_3$ EFFECT IN RAT | | COMPETITIVE BINDING TO 1,25-$(OH)_2D_3$ RECEPTORS | | |
|---|---|---|---|---|---|---|
| | | INTESTINAL | BONE | % of 1,25-$(OH)_2D_3$ EFFECT | | |
| Compound | CONCENTRATION NG/RAT | CALCIUM ABSORPTION | CALCIUM MOBILIZATION | RAT INTESTINE | CHICK INTESTINE | CALF INTESTINE |
| 1,25-$(OH)_2D_3$ | 12.5 | 100 | 100 | 100 | 100 | 100 |
| 1,25-$(OH)_2D_3$-Hexa $^2H$ | 12.5 | 92 | 64 | 100 | 106 | 100 |
| 1,25-$(OH)_2D_3$-Octa $^2H$ | 12.5 | 106 | 147 | | 104 | 76 | resulting plasma was measured for calcium concentration by atomic absorption spectroscopy. Since rats were fed a diet essentially devoid of Ca, plasma Ca increases reflected mobilization of Ca from bone, not intestinal Ca absorption.

All data (intestinal and bone) were expressed relative to 1,25-$(OH)_2D_3$ using the following formula:

$$\text{Response } (ICA \text{ or } BCM) = \frac{x-z}{y-z} \times 100$$

where x is the response elicited by the test compound, y is the response elicited with 1,25-$(OH)_2D_3$, and z is the response in the control animals.

COMPETITIVE BINDING TO 1,25-$(OH)_2D_3$ INTESTINE RECEPTORS

Experimental Procedures

The ability of vitamin $D_3$ metabolites to compete for 1,25-$(OH)[^3H]D_3$ receptor binding sites was evaluated with receptor prepared from intestine of chick, rat and calf. The receptor was prepared by removing 10-12% of the small intestine immediately adjacent to the pyloric spincter which was washed immediately with cold buffer containing 500 mM KCl, 50 mM Tris, 1.5 mM EDTA, and 5 mM dithiothreitol, pH 7.4 (KTED buffer). Mucosa was collected and washed three times with 10 volumes of cold KTED buffer. The washed mucosa was homogenized in KTED buffer (20% w/v) using a Polytron Pt20 tissue disruptor. Cytosol was prepared by centrifugation of the homogenized mucosa at 300,000 × g for 1 hour. Receptor was precipitated from the cytosol by the addition of ammonium sulphate to achieve 35% saturation. The ammonium sulphate

EVALUATION OF 1,25-DIHYDROXYCHOLECALCIFEROL AND OF 1,25-DIHYDROXY-26,27-HEXADEUTERO-CHOLECALCIFEROL IN VITAMIN D DEFICIENT RATS

Experimental Procedures

Rats were placed on the following protocol.

D+ Control

Ten 3 week old rats were maintained on vitamin $D_3$ replete diet for 6 weeks.

D- Control

Ten 3 week old rats were maintained on vitamin $D_3$ deficient diet for 6 weeks.

Low Dose Treatment

One hundred 3 week old rats were maintained for 3 weeks on vitamin $D_3$ deficient diet, and the following 3 weeks treated with a low dose (See Table III) of 1,25-$(OH)_2D_3$ or 1,25-$(OH)_2D_3$-Hexa $^2H$, while maintaining the same diet.

High Dose Treatment

One hundred 3 week old rats were maintained for 3 weeks on vitamin $D_3$ deficient diet, and the following 3 weeks treated with a high dose (See Table III) of 1,25-$(OH)_2D_3$ or 1,25-$(OH)_2D_3$-Hexa $^2H$, while maintaining the same diet.

The following parameters in Table III were evaluated, by means which are conventional in the art, after completion the above treatments. Bone mass is measured by known histomorphometric methods.

TABLE III

| | Daily Dose ng | Body Weight gr | Serum $Ca^{2+}$ mg/dl | Serum $PO_4^{2-}$ mg/dl | Serum Creatinine mg/dl | Bone Mass $mm^3/cm^3$ |
|---|---|---|---|---|---|---|
| 1,25-(OH)$_2$D$_3$ | 15 | 192 ± 4.5 | 11.87 ± 0.16 | 7.61 ± 0.31 | 0.37 ± 0.04 | 156 ± 16 |
| | 60 | 156 ± 15 | 11.92 ± 0.40 | 6.58 ± 0.30 | 0.35 ± 0.02 | 296 ± 56 |
| 1,25-(OH)$_2$D$_3$-Hexa $^2$H | 16.5 | 193 ± 5 | 11.28 ± 0.26 | 7.08 ± 0.07 | 0.36 ± 0.02 | 288 ± 58 |
| | 66 | 163 ± 7.2 | 11.20 ± 0.28 | 6.61 ± 0.36 | 0.36 ± 0.04 | 371 ± 68 |
| D− control | | 184 ± 1.3 | 5.60 ± 0.5 | 8.65 ± 0.6 | 0.44 ± 0.04 | 96.5 ± 9 |
| D+ control | | 202 ± 3.1 | 10.41 ± 0.10 | 5.76 ± 0.12 | 0.41 ± 0.01 | 168 ± 15 |

In the above Tables:

1,25-(OH)$_2$D$_3$ is 1α,25-dihydroxycholecalciferol;

1,25-(OH)$_2$D$_3$-Hexa $^2$H is 26,26,26,27,27,27 hexadeutero-1α,25-dihydroxycholecalciferol; and 1,25-(OH)$_2$D$_3$-Octa $^2$H is 24,24,26,26,26,27,27,27-octadeutero-1α,25-dihydroxycholecalciferol.

The data in Table I above show that the deuterated compounds of the invention stimulate avian and porcine cartilage formation and thus demonstrate that said compounds stimulate new bone formation. The bone mass data in Table III show that 1,25-(OH)$_2$ D$_3$-Hexa$^2$H is more active than 1,25-(OH)$_2$D$_3$ in increasing bone mass. Moreover, the serum Ca$^2$+data in Table III show that the compound 1,25-(OH)$_2$D$_3$-Hexa$^2$H of the invention is not as active as 1,25-(OH)$_2$D$_3$ in inducing hypercalcemia. The data in Table II show that the compounds of the invention are comparable to 1,25-(OH)$_2$D$_3$ in inducing intestinal calcium absorption, bone calcium mobilization, and in competing for 1,25-(OH)$_2$D$_3$ receptors.

The compounds of formula I can be formulated in compositions such as tablets, capsules and the like, or elixirs for oral administration, or in sterile solutions or suspensions for parenteral administration, or in topical formulations. About 0.25 to about 2 μg of a compound of formula I can be compounded with a pharmaceutically acceptable vehicle, carrier, excipient, binder, preservative, stabilizer, flavor and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; an excipient such as dicalcium phosphate; a disintegrating agent such as corn starch, potato starch, algenic acid and the like; a lubricant such as magnesium stearate a sweetening agent such as sucrose, lactose or saccharin; a flavoring agent such as peppermint, oil of wintergreen or cherry. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle, such as water for injection, a naturally occurring vegetable oil, such as sesame oil, coconut oil, peanut oil, cottonseed oil, and the like, or a synthetic fatty vehicle such as ethyl oleate or the like. Buffers, preservatives, anti-oxidants and the like can be incorporated as required.

Compositions for topical administration can be prepared by conventional means, and, in particular, as illustrated in examples given below.

The examples which follow further illustrate the disclosure. All temperatures are in degrees Celsius unless otherwise stated.

EXAMPLE 1

Preparation of
[3aS-[3(βS*,δR*),3aα,7β,7aβ]]-7-(acetyloxy)-β-chloro-3a,4,5,6,7,7a-hexahydro-δ,3a-dimethyl-1H-indene-3-butanol A solution of 1.01 g (2.95 mmol) of [3aS-[3(αS*,γR*)-,3aα,7β,7aβ]-7-(acetyloxy)-α-chloro-3a,4,5,6,7,7a-hexahydro-γ,3a-dimethyl-1H-indene-3-butanoic acid methyl ester in 25 mL of anhydrous tetrahydrofuran was cooled at 0° C. and treated under argon with 1.47 mL (1.47 mmol) of a 1M solution of lithium aluminum hydride in tetrahydrofuran. After stirring for 2 hours at 0° C., additional 0.20 mL of lithium aluminum hydride solution was added and the reaction allowed to proceed for 1 additional hour. It was then quenched by careful addition of 8 mL of a 2N aqueous Rochelle salt solution, then 0.5 mL of 2N hydrochloric acid. After dilution with water, it was extracted with ethyl acetate. The combined extracts were washed with 2N aqueous Rochelle salt solution, then brine, dried and evaporated to dryness to give 0.90 g (93% yield) of the title compound as a colorless, thick oil: [α]$^{23}$D −30.1° (c 0.6, EtOH); $^1$H NMR (200 MHz, CDCl$_3$) δ0.93 (s, 3H), 1.07 (d, J=7.2 Hz, 3H), 2.04 (s, 3H), 2.52 (br m, 1H), 3.73 (m, 2H), 4.00 (m, 1H), 4.97 (td, J=12.0, 4.4 Hz, 1H), 5.27 (br s, 1H) ppm.

EXAMPLE 2

Preparation of
[3aS-[3(1R*,3S*),3aα,7β,7aβ]]-7-(acetyloxy)-3-(3-chloro-4-bromo-1-methylbutyl)-3a,4,5,6,7,7a-hexahydro-3a-methyl-1H-indene A solution of 1.50 g (4.76 mmol) of [3aS-[3(βS*,δR*),3aα,7β,7aβ]]-7-(acetyloxy)-β-chloro-3a,4,5,6,7,7a-hexahydro-δ,3a-dimethyl-1H-indene-3-butanol in 20 mL of dichloromethane and 20 mL of pyridine was treated at 0° C. and under argon with 4.50 g (23.60 mmol) of p-toluenesulfonyl chloride and then stirred overnight at 0° C. Water (8 mL) was then added and, after stirring the resulting mixture for 1 hour at room temperature, the solvents were removed in vacuo and the residue diluted with water and extracted with ethyl acetate. The combined organic extracts were subsequently washed with 1N hydrochloric acid, water, 2N aqueous potassium bicarbonate solution and brine and dried. The residue obtained after evaporation of the ethyl acetate (weighing 2.10 g) was dissolved in 40 mL of N,N-dimethylformamide and heated under argon at 50° C. with 4.00 g (46.06 mmol) of anhydrous lithium bromide for 17 hours. After cooling, the reaction mixture was diluted with ice water and extracted with ethyl acetate. The combined organic extracts were washed several times with water, dried and evaporated to dryness to give 1.62 g (90% overall yield) of the title compound. $^1$H NMR (60 MHz, CDCl$_3$) δ0.88 (s, 3H), 1.07 (d, J=6.4 Hz, 3H), 2.03 (s, 3H), 3.60 (br AB q, J=10.2 Hz, Δγ=14.0 Hz, 2H), 5.00 br m, 1H), 5.33 (br s, 1H) ppm.

EXAMPLE 3

Preparation of
[3aS-[3(R*),3aα,7β,7aβ]]-3a,4,5,6,7,7a-Hexahydro-3a-methyl-3-(1-methyl-3-butynyl)-1H-indene-7-ol A suspension of 1.40 g (35.89 mmol) of sodium amide in 15 mL of hexamethylphosphoramide was first treated under argon with 1.10 mL (11.66 mmol) of tert-butyl alcohol, over a 5 minute period, then with a solution of 1.31 g (3.46 mmol) of [3aS-[3(1R*,3S*),3aα,7β,7aβ]]-7-(acetyloxy)-3-(3-chloro-4-bromo-1-methylbutyl)-3a,4,5,6,7,7a-hexahydro-3a-methyl-1H-indene in 20 mL of hexamethylphosphoramide and the resulting mixture stirred at room temperature for 2.5 hours. It was then quenched by careful addition of iced saturated aqueous ammonium chloride solution, followed by acidification with 2N hydrochloric acid and extraction with ethyl acetate. The combined organic layers were washed with saturated ammonium chloride solution, then several times with water, dried and evaporated in vacuo. The residue was purified by chromatography on silica (using hexane-ethyl acetate 2:1 as solvent) to give 0.27 g (36% yield) of the title compound as colorless, thick oil: [α]$^{25}$D −4.1° (c 0.5, EtOH); $^1$H NMR (200 MHz, CDCl$_3$) δ0.81 (s, 3H), 1.05 (d, J=6.0 Hz, 3H), 2.32 (br s, 1H), 3.81 (td, J=10.4, 4.8 Hz, 1H), 5.44 (br s, 1H) ppm.

EXAMPLE 4

Preparation of
[3aS-[3(R*),3aα,7β,7aβ]]-3a,4,5,6,7,7a-hexahydro-3a-methyl-3-(1-methyl-3-butynyl)-7-[(trimethylsilyl)oxy]-1H-indene A solution of 0.680 g (3.11 mmol) of [3aS-[3(R*),3aα,7β,7aβ]]-3a,4,5,6,7,7a-hexahydro-3a-methyl-3-(1-methyl-3-butynyl)-1H-indene-7-ol in 15 mL of anhydrous tetrahydrofuran was treated with 0.700 mL of 1-(trimethylsilyl)imidazole (4.77 mmol) and the resulting mixture stirred at room temperature, under argon, for 2 hours. The solvent was then evaporated to dryness and the residue applied to a silica column, eluted with hexane-ethyl acetate (10:1) to give 0.845 g (94% yield) of the title compound as a thick oil, which was immediately used in the next step.

EXAMPLE 35

Preparation of
[3aS-[3(R*),3aα,7β,7aβ]]-5-(3a,4,5,6,7,7a-Hexahydro-7-hydroxy-3a-methyl-1H-inden-3-yl)-5-methyl-2-pentynoic acid methyl ester A solution of 0.400 g (1.38 mmol) of [3aS-[3(R*),3aα,7β,7aβ]]-3a,4,5,6,7,7a-hexahydro-3a-methyl-3-(1-methyl-3-butynyl)-7-[(trimethylsilyl)oxy]-1H-indene in 8 mL of anhydrous tetrahydrofuran was treated dropwise at −78° C. and under argon with 1.05 mL (1.68 mmol) of a 1.6M solution of n-butyllithium in hexane. After stirring for 30 minutes at −78° C., the resulting solution was slowly transferred via cannula to a stirred solution of 0.225 mL (2.91 mmol) of methyl chloroformate in 2 mL of anhydrous tetrahydrofuran, also at −78° C. and under argon. After the addition was completed, the resulting mixture was allowed to come to room temperature, during a 1 hour period and then stirred for an additional 1 hour. It was then slowly treated with 5 mL of a 5% aqueous sodium dihydrogen phosphate solution, stirred for 15 minutes and extracted with ethyl acetate. The combined organic phases were washed with 2N hydrochloric acid, water and brine, dried and evaporated to dryness. The residue was purified by rapid chromatography through silica (eluent: hexane-ethyl acetate 2:1) to give 0.348 g (91% yield) of the title compound as a colorless, thick oil: [α]$^{25}$D −7.1° (c 0.4, EtOH); $^1$H NMR (100 MHz, CDCl$_3$) δ0.81 (s, 3H), 1.16 (d, J=6.8 Hz, 3H), 3.60 to 4.00 (m, 1H), 3.76 (s, 3H), 5.42 (br s, 1H) ppm.

EXAMPLE 6

Preparation of
[1R-[1α(R*),3aβ,4β,7aα]]-octahydro-δ,7a-dimethyl-4-hydroxy-1H-indene-1-pentanoic acid methyl ester A solution of 0.300 g (1.09 mmol) of [3aS-[3(R*),3aα,7β,7aβ]]-5-(3a,4,5,6,7,7a-hexahydro-7-hydroxy-3a-methyl-1H-inden-3-yl)-5-methyl-2-pentynoic acid methyl ester in 20 mL of ethanol was treated with 0.100 g of 5% palladium on carbon catalyst and the mixture hydrogenated under atmospheric pressure overnight. Filtration of the catalyst and evaporation of the solvent gave 0.294 g (96% yield) of the title compound as a colorless, thick oil: [α]$^{25}$D +11.6 (c 0.2, EtOH); $^1$H NMR (400 MHz, CDCl$_3$) δ0.68 (s, 3H), 0.93 (d, J=7.2 Hz, 3H), 2.30 (m, 2H), 3.60 (m, 1H), 3.69 (s, 3H) ppm.

EXAMPLE 7

Preparation of
[1R-[1α(R*)3aβ,4β,7aα]]-octahydro-ε,7a-dimethyl-α,α-(dimethyl-d$_3$)-4-hydroxy-1H-indene-1-pentanol An ether solution of 2 mL (3.00 mmol) of freshly prepared methyllithium-d$_3$ was diluted with 6 mL of anhydrous ether and treated dropwise at 0° C., under argon, with 0.147 g (0.52 mmol) of [1R-[1α(R*)-,3aβ,4β,7aα]]-octahydro-δ,7a-dimethyl-4-hydroxy-1H-indene-1-pentanoic acid methyl ester, dissolved in 2.5 mL of anhydrous tetrahydrofuran. After stirring at 0° C. for 40 minutes, an additional 0.5 mL (0.75 mmol) of methyllithium-d$_3$ solution was added and the mixture allowed to react for an additional 25 minutes. It was then quenched with a mixture of 2 mL of 2N potassium bicarbonate and 2 mL of Rochelle salt solutions, allowed to come to room temperature and extracted with ethyl acetate. The combined organic extracts were washed with 2N potassium bicarbonate then brine, dried and evaporated to dryness. The residue was purified by rapid chromatography through silica (using hexane-ethyl acetate 1:1 as eluant) to give 0.119 mg (79% yield) of the title compound as a white solid. $^1$H NMR (100 MHz, CDCl$_3$) δ0.68 (s, 3H), 0.93 (d, J=6.0 Hz, 3H), 3.57 (m, 1H) ppm.

EXAMPLE 8

Preparation of
[1R-[1α(R*),3β,7aα]]-octahydro-1-[5-[(trimethylsilyl)oxy]-1-methyl-5-(methyl-$d_3$)-6,6,6-$d_3$-hexyl]-7a-methyl-4H-inden-4-one A solution of 0.117 g (0.406 mmol) of [1R-[1α(R*)3aβ,4β,7aα]]-octahydro-ε,7a-dimethyl-α,α-(dimethyl-$d_3$)-4-hydroxy-1H-indene-1-pentanol in 6 mL of methylene chloride was stirred at room temperature with 0.270 g (1.253 mmol) of pyridinium chlorochromate for 2.5 hours. The resulting dark brown suspension was diluted with ether, filtered over Celite ® filter aid and the residue triturated with ether and filtered. The combined filtrates were evaporated to dryness and the crude residue purified by rapid chromatography through silica (eluant: hexane-ethyl acetate 2:1). The obtained product (0.105 g) was dissolved in 6 mL of methylene chloride, treated with 0.225 mL (1.534 mmol) of 1-(trimethylsilyl)imidazole and stirred under argon at room temperature for 16 hours. Water (2 mL) was then added and, after stirring for 20 minutes, the resulting mixture extracted with ethyl acetate. The combined extracts were washed with water and brine, dried and evaporated to dryness. The residue was purified by fast filtration through silica, eluting with hexane-ethyl acetate (5:1) to give 0.120 g (82% overall yield) of the title compound as a colorless liquid.

EXAMPLE 9

Preparation of
26,26,26,27,27,27-hexadeutero-1α,25-dihydroxycholecalciferol

A solution of 0.284 g (0.488 mmol) of 3S-(1Z,5α,5β)]-[2[3,5-bis[[(1,1-dimethylethyl)dimethylsilyl]oxy]-2-methylenecyclohexylidene]ethyl]diphenylphosphine oxide in 8 mL of anhydrous tetrahydrofuran was cooled at −78° C. and treated dropwise under argon with 0.295 mL (0.472 mmol) of a 1.6M solution of n-butyllithium in hexane. The resulting deep red solution was stirred for 5 minutes, then treated dropwise at −78° C. with a solution of 0.120 g (0.334 mmol) of [1R-[1α(R*),3aβ,7aα]]-octahydro-1-[5-[(trimethylsilyl)oxy]-1-methyl-5-(methyl-$d_3$)-6-$d_3$-hexyl]-7a-methyl-4H-inden-4-one in 3 mL of anhydrous tetrahydrofuran over 10 minutes and the stirring was continued under argon at −78° C. for 2 hours. After addition of 3 mL of a 1:1 mixture of 2N Rochelle salt solution and 2N potassium bicarbonate, the reaction mixture was allowed to come to room temperature and extracted with ethyl acetate. The combined organic extracts were washed with brine, dried and evaporated to dryness. The residue was purified by fast filtration through silica (eluant: hexane-ethyl acetate 30:1) to give 0.217 g of the title compound. This was dissolved in a mixture of 1 mL of methylene chloride and 8 mL of methanol, treated with 3.0 g of AG 50W-X4 cation exchange resin (Bio-Rad Laboratories, Richmond, Calif. 94804) and the resulting suspension stirred under argon at room temperature for 18 hours. After filtration and washing of the resin with methanol, the combined filtrates were evaporated to dryness. The residue was purified by rapid chromatography through silica (eluting with hexane-ethyl acetate 1:4) to give 0.112 g (79% overall yield) of the title compound as a white solid, mp 117°–118° C. (after recrystallization from methyl formate): [α]$^{25}$D +43.3° (c 0.2, EtOH); $^1$H NMR (200 MHz, CDCl$_3$) δ0.54 (s, 3H), 0.94 (d, J=6.0 Hz, 3H), 4.22 (br, 1H), 4.43 (br m, 1H), 4.99 (br s, 1H), 5.43 (br s, 1H), 6.03 (d, J=11.6 Hz, 1H), 6.36 (d, J=11.6 Hz, 1H); mass spectrum: 96.3% $d_6$, 3.6% $d_5$.

EXAMPLE 10

Preparation of
[1R-[1α(R*),3aβ,4β,7aα]]-octahydro-α,α,$d_2$-δ,7a-dimethyl-4-hydroxy-1H-indene-1-pentanoic acid methyl ester A solution of 0.288 g (1.020 mmol) of [1R-[1α(R*),3aβ,4β,7aα]]-octahydro-δ,7a-dimethyl-4-hydroxy-1H-indene-1-pentanoic acid methyl ester, dissolved in 5 mL of methyl-$d_3$ alcohol-d was treated with 0.1 mL of a 3N solution of sodium methoxide-$d_3$ in methyl-$d_3$ alcohol-d and the resulting mixture refluxed under argon for 9 hours, then heated at 50° C. overnight. The base present was then neutralized by addition of AG 50W-X4 cation exchange resin (Bio-Rad Laboratories, Richmond, Calif. 94804), then filtered and after washing of the resin with methanol, the combined filtrates evaporated to dryness. The residue was purified by rapid chromatography through silica (eluting with hexane-ethyl acetate 2:1). The obtained product (0.154 g) was dissolved in 5 mL of methyl-$d_3$ alcohol-d in the presence of 0.1 mL of 3N sodium methoxide-$d_3$ in methyl-$d_3$ alcohol-d, refluxed for 4 hours and worked up and purified as described above to give 0.066 g (23% yield) of the title compound as a colorless oil.

EXAMPLE 11

Preparation of
[1R-[1α(R*),3aβ,4β,7aα]]-octahydro-ε,7a-dimethyl-β,β-$d_2$-α,α-(dimethyl-$d_3$)-4-hydroxy-1H-indene-1-pentanol Using the procedure described in Example 7, 0.065 g of [1R-[1α(R*),3aβ,4β,7aα]]-octahydro-α,α-$d_2$-δ,7a-dimethyl-4-hydroxy-1H-indene-1-pentanoic acid methyl ester was converted to 0.049 g (75% yield) of the title compound, as a white solid.

EXAMPLE 12

Preparation of
[1R-[1α(R*),3aβ,7aα]]-octahydro-1-[5-[(trimethylsilyl)oxy]-1-methyl-5-(methyl-$d_3$)-4,4,6,6,6-$d_5$-hexyl]-7a-methyl-4H-inden-4-one Using the procedure described in Example 8, 0.047 g of [1R-[1α(R*),3aβ,4β,7aα]]-octahydro-ε,7a-dimethyl-β,β-$d_2$-α,α-(dimethyl-$d_3$)-4H-hydroxy-1H-indene-1-pentanol was converted to 0.051 g of the title compound, as a colorless oil.

EXAMPLE 13

Preparation of
24,24,26,26,26,27,27,27-octadeutero-1α,25-dihydroxycholecalciferol Using the procedure described in Example 9, 0.051 g of [1R-[1α(R*),3aβ,7aα]]-octahydro-1-[5-[(trimethylsilyl)oxy]-1-methyl-5-(methyl-$d_3$)-4,4,6,6,6-$d_5$-hexyl]-7a-methyl-4H-inden-4-one was converted to 0.050 g (83% overall yield) of the title compound as a white, crystalline material, mp 104°–107° C.; mass spectrum: 95.8% $d_8$, 2.2% $d_4$; 1.0%-$d_3$.

EXAMPLE 14

CAPSULE FORMULATION

|  | mg/cap | |
| --- | --- | --- |
| 24,24,26,26,26,27,27,27-octadeutero-1α,25-dihydroxycholecalciferol | 0.000250 | 0.002 |
| Fractionated Coconut Oil | 199.995 | 199.990 |
| Butylated Hydroxy Anisol | 0.01 | 0.01 |
| Ascorbyl Palmitate | 1.0 | 1.0 |

1. Dissolve the drug in Fractionated Coconut Oil.
2. Add Butylated Hydroxy Anisol and Ascorbyl Palmitate to the solution in Step 1 and dissolve.
3. Fill in Soft Gelatin Capsules.

EXAMPLE 15

CAPSULE FORMULATION

|  | mg/cap | |
| --- | --- | --- |
| 26,26,26,27,27,27-hexadeutero-1α,25-dihydroxycholecalciferol | 0.00025 | 0.002 |
| Fractionated Coconut Oil | 199.995 | 199.990 |
| Butylated Hydroxy Anisol | 0.01 | 0.01 |
| Ascorbyl Palmitate | 1.0 | 1.0 |

1. Dissolve the drug in Fractionated Coconut Oil.
2. Add Butylated Hydroxy Anisol and Ascorbyl Palmitate to the solution in Step 1 and dissolve.
3. Fill in Soft Gelatin Capsules.

EXAMPLE 16

CREAM 0.00001% and 0.001%

| Quantitative Composition: | g/kg | g/kg |
| --- | --- | --- |
| 24,24,26,26,26,27,27,27-1α,25-dihydroxycholecalciferol | 0.0001 | 0.01 |
| Glyceryl Mono Stearate | 100.001 | 100.000 |
| Polysorbate 80 | 20.00 | 20.00 |
| Cetyl Alcohol | 50.00 | 50.00 |
| Petrolatum | 70.00 | 70.00 |
| Methyl Paraben | 1.50 | 1.50 |
| Propyl Paraben | 0.50 | 0.50 |
| Propylene Glycol | 200.00 | 200.00 |
| Purified Water | 568.05 | 568.05 |

1. Dissolve drug in Propylene Glycol. Add Methyl Paraben, Propyl Paraben and Water. Heat to 70° C.
2. Melt Glyceryl Mono Stearate, Cetyl Alcohol and Petrolatum. Add Polysorbate 80 and heat to 70° C.
3. Mix Step 1 with Step 2 with continuous stirring. Cool to room temperature.

EXAMPLE 17

CREAM 0.00001% and 0.001%

| Quantitative Composition: | g/kg | g/kg |
| --- | --- | --- |
| 26,26,26,27,27,27-hexadeutero-1α,25-dihydroxycholecalciferol | 0.0001 | 0.01 |
| Glyceryl Mono Stearate | 100.00 | 100.00 |
| Polysorbate 80 | 20.00 | 20.00 |
| Cetyl Alcohol | 50.00 | 50.00 |
| Petrolatum | 70.00 | 70.00 |
| Methyl Paraben | 1.50 | 1.50 |
| Propyl Paraben | 0.50 | 0.50 |
| Propylene Glycol | 200.00 | 200.00 |
| Purified Water | 568.05 | 568.05 |

1. Dissolve drug in Propylene Glycol. Add Methyl Paraben, Propyl Paraben and Water. Heat to 70° C.
2. Melt Glyceryl Mono Stearate, Cetyl Alcohol and Petrolatum. Add Polysorbate 80 and heat to 70° C.
3. Mix Step 1 with Step 2 with continuous stirring. Cool to room temperature.

We claim:

1. A compound of the formula

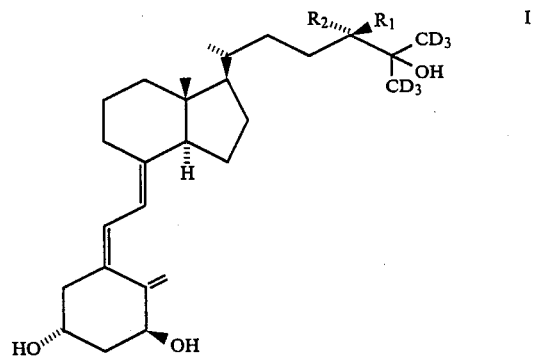

wherein $R_1$ and $R_2$ are deuterium.

2. A process for preparing a compound of formula

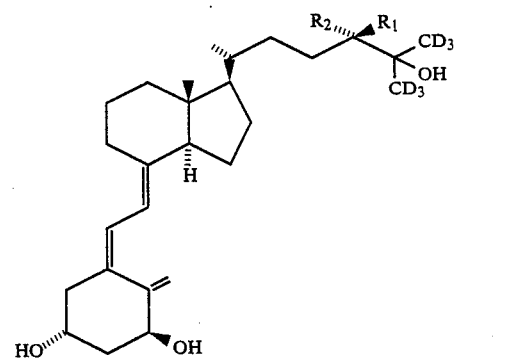

wherein $R_1$ and $R_2$ are either both hydrogen or both deuterium, which comprises the step of reacting a compound of formula

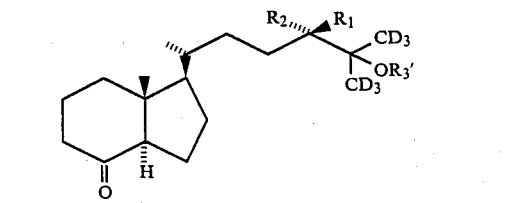

wherein $R_1$ and $R_2$ are as described above $R_3'$ is Si-(Alk)$_3$ wherein Alk is lower alkyl; with a compound of the formula

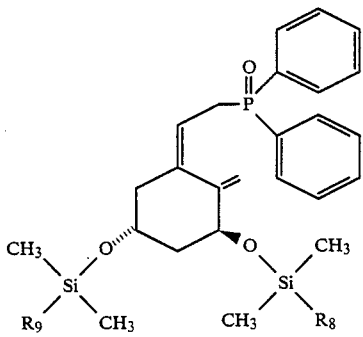

XI wherein R$_8$ and R$_9$ are lower alkyl or aryl to yield a compound of the formula

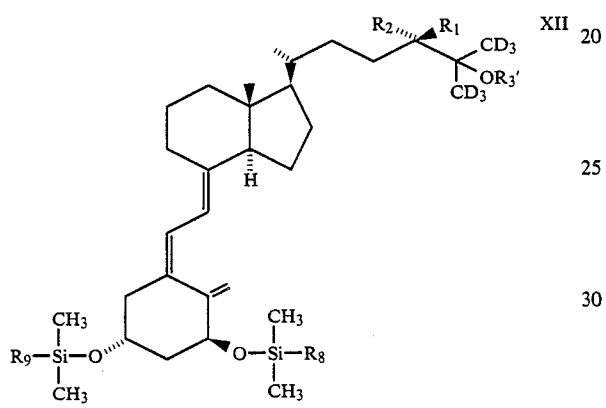

XII wherein R$_1$, R$_2$, R$_3'$, R$_8$, and R$_9$, are described above and removing the protecting groups from the compound of formula XII.

3. A process in accordance with claim 2, wherein R'$_3$ is Si(CH$_3$)$_3$.

4. A process in accordance with claim 3, wherein the compound of formula X is [1R-[1α(1R*),3aβ,7aα]]-octahydro-1-[5-[(trimethylsilyl)oxy]-1-methyl-5-(methyl-d$_3$)-4,4,6,6,6-d$_5$-hexyl]-7a-methyl-4H-inden-4-one and the compound of formula XI is [3S-(1Z,5α,5β)]-[2[3,5-bis [[(1,1-dimethylethyl)dimethylsilyl]oxy]-2-methylenecyclohexylidene]ethyl]diphenylphosphine oxide.

5. A method for treating osteoporosis which comprises administering an effective amount of a compound of the formula

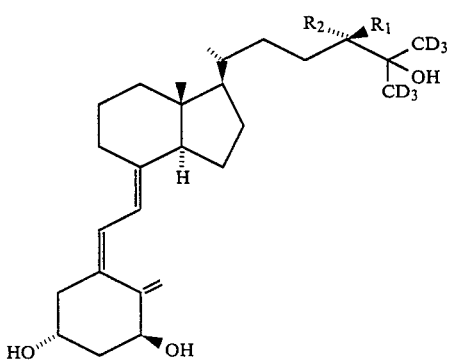

I wherein R$_1$ and R$_2$ are either both hydrogen or both deuterium.

6. A method in accordance with claim 5, wherein the compound of formula I is 26,26,26,27,27,27-hexadeutero-1α,25-dihydroxycholecalciferol.

7. A method in accordance with claim 5, wherein the compound of formula 1 is 24,24,26,26,26,27,27,27-octadeutero-1α,25-dihydroxycholecalciferol.

8. A method in accordance with claim 5, wherein the compound of formula I is administered in a dosage of from about 0.25 μg to about 2 μg.

9. A method for treating cutaneous inflammations which comprises administering an effective amount of a compound of the formula

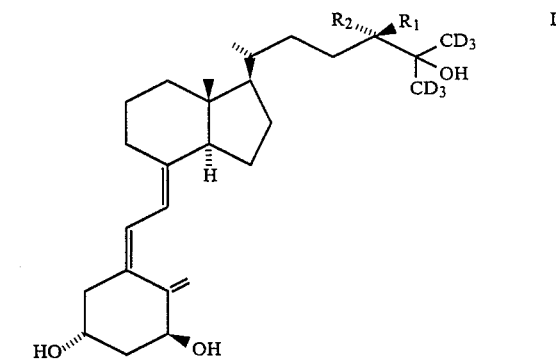

I wherein R$_1$ and R$_2$ are either both hydrogen or both deuterium.

10. A method according to claim 9, wherein the cutaneous inflammation is psoriasis.

11. A method in accordance with claim 10, wherein the compound of formula I is administered topically.

12. A method in accordance with claim 11, wherein the compound of formula I is 26,26,26,27,27,27-hexadeutero-1α,25-dihydroxycholecalciferol.

13. A method in accordance with claim 11, wherein the compound of formula I is 24,24,26,26,26,27,27,27-octadeutero-1α,25-dihydroxycholecalciferol.

14. A composition comprising a pharmaceutically effective amount of a compound of the formula

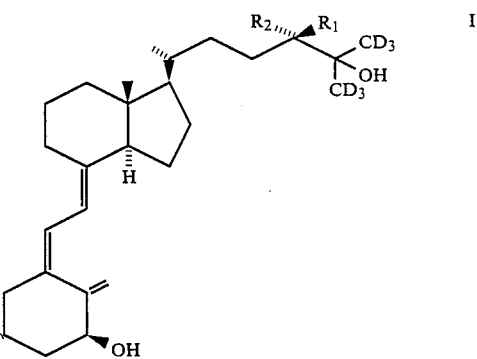

I wherein R$_1$ and R$_2$ are either both hydrogen or both deuterium, and a pharmaceutically acceptable carrier material.

15. A composition in accordance with claim 14, wherein the compound of formula I is 26,26,26,27,27,27-hexadeutero-1α,25-dihydroxycholecalciferol.

16. A composition in accordance with claim 14, wherein the compound of formula I is 24,24,26,26,26,27,27,27-octadeutero-1α,25-dihydroxycholecalciferol.

* * * * *